(12) United States Patent
Zheng et al.

(10) Patent No.: US 11,946,073 B2
(45) Date of Patent: Apr. 2, 2024

(54) METHOD FOR NON-ENZYMATIC 3D CULTURE AND AMPLIFICATION OF MESENCHYMAL STEM CELLS

(71) Applicants: Healthina Stem Cell Industry Platform (Tianjin) Limited, Tianjin (CN); Tangyi Holdings(Shenzhen) Limited, Shenzhen (CN)

(72) Inventors: Bin Zheng, Tianjin (CN); Yulin Cao, Beijing (CN); Wenchang Peng, Tianjin (CN); Shixiang Cheng, Tianjin (CN)

(73) Assignees: Healthina Stem Cell Industry Platform (Tianjin) Limited, Tianjin (CN); Tangyi Holdings(Shenzhen) Limited, Shenzhen (CN)

( * ) Notice: Subject to any disclaimer, the term of this patent is extended or adjusted under 35 U.S.C. 154(b) by 30 days.

(21) Appl. No.: 17/739,127

(22) Filed: May 8, 2022

(65) Prior Publication Data

US 2023/0287352 A1    Sep. 14, 2023

(30) Foreign Application Priority Data

Mar. 9, 2022   (CN) .......................... 202210226396.6

(51) Int. Cl.
*C12N 5/0775* (2010.01)
*A61K 9/16* (2006.01)
*C12N 5/00* (2006.01)

(52) U.S. Cl.
CPC .......... *C12N 5/0663* (2013.01); *A61K 9/1647* (2013.01); *A61K 9/1652* (2013.01); *A61K 9/1694* (2013.01); *C12N 5/0075* (2013.01)

(58) Field of Classification Search
CPC ................ C12N 5/0663; C12N 5/0075; C12N 2531/00; C12N 2513/00; C12N 2533/40; C12N 2539/10; C12N 5/0662; A61K 9/1647; A61K 9/1652; A61K 9/1694; A61K 9/06; A61K 31/12; A61K 31/121; A61K 31/00; A61K 47/02; A61K 9/5153; A61L 27/20; A61L 27/56; A61L 27/3834; A61L 27/446; A61L 2300/64; A61L 2430/02; C08J 9/28; C08J 2367/04
See application file for complete search history.

(56) References Cited

FOREIGN PATENT DOCUMENTS

| CN | 106727430 A | * | 5/2017 | .............. A61K 31/12 |
| CN | 107468638 A | * | 12/2017 | ......... A61K 31/4748 |

OTHER PUBLICATIONS

Zhang et al. (Chinese Journal of Polymer Science vol. 32, No. 12, (2014), 1590-1601 doi: 10.1007/s10118-014-1551-5) (Year: 2014).*
Qutachi et al. (Acta Biomaterialia 10 (2014) 5090-5098 http://dx.doi.org/10.1016/j.actbio.2014.08.015) (Year: 2014).*
Lee et al. (Biomacromolecules 2002, 3, 1115-1119 https://doi.org/10.1021/bm020066h) (Year: 2002).*
M. El-Zaafarany et al. (Pharmaceutics 2018, 10, 217; doi:10.3390/pharmaceutics10040217) (Year: 2017).*
Mohammadpour et al. (Journal of Pharmaceutical Innovation (2022) 17:712-724, https://doi.org/10.1007/s12247-021-09544-7) (Year: 2022).*
Oliveira et al. (Journal of Nanoparticle Research vol. 22, Article No. 115 (2020) https://doi.org/10.1007/s11051-020-04832-8) (Year: 2020).*
Liu et al. (Polymers 2022, 14(5), 993; https://doi.org/10.3390/polym14050993 Published: Feb. 28, 2022 ) (Year: 2022).*
Yan et al. (RSC Adv., 2017, 7, 14888-14901 DOI: 10.1039/c7ra00631d) (Year: 2017).*
Krinner et al., 2009 (Cell Prolif. 2009, 42, 471-484, doi: 10.1111/j.1365-2184.2009.00621.x). (Year: 2009).*

* cited by examiner

*Primary Examiner* — Janet L Epps-Smith
*Assistant Examiner* — Khoa Nhat Tran
(74) *Attorney, Agent, or Firm* — PORUS IP LLC

(57) ABSTRACT

A method for non-enzymatic 3D culture and amplification of mesenchymal stem cells (MSCs) includes the followings steps: preparing PLGA porous microspheres; preparing a PLGA-PEG-PLGA thermosensitive coating microcarrier; culturing and amplifying MSCs; and performing non-enzymatic separation of MSCs, including reducing a culture temperature to below a critical phase transition temperature, and centrifuging a culture medium to collect stem cells. The present invention adopts the method for non-enzymatic 3D culture and amplification of MSCs, wherein the PLGA porous microspheres are used as a cell culture microcarrier scaffold and the thermosensitive hydrogel PLGA-PEG-PLGA is coated on surfaces of such microspheres, without needing additional enzymolysis process, thus efficiently amplifying the stem cells.

4 Claims, 2 Drawing Sheets

METHOD FOR NON-ENZYMATIC 3D CULTURE AND AMPLIFICATION OF MESENCHYMAL STEM CELLS

CROSS REFERENCE TO THE RELATED APPLICATIONS

This application is based upon and claims priority to Chinese Patent Application No. 202210226396.6, filed on Mar. 9, 2022, the entire contents of which are incorporated herein by reference.

TECHNICAL FIELD

The present invention relates to the technical field of mesenchymal stem cell (MSC) culture, in particular to a method for non-enzymatic 3D culture and amplification of MSCs.

BACKGROUND

Cell therapy is expected to change a variety of diseases, including cancers, neurodegenerative diseases and autoimmune diseases, by using human cells as drugs, through complex mechanisms that cannot be achieved by a single compound. The cell therapy, on the other hand, may be the result of a "population effect", in which cells required for regeneration or immune process in the body need to be present in large numbers. Therefore, only by increasing the number of therapeutic cells in pathological state can the balance of therapy be tipped towards repair. In these cases, an amplification of a sufficient number of cells is essential to provide an effective therapeutic dose.

At present, suspension culture and adhesion culture are the two main methods for amplifying MSCs. The suspension culture features a high space efficiency and high yield. In contrast, the traditional 2D culture method of adherent cells requires a large plane area for cell growth and amplification, which is less economical. It is clear that 2D culture systems are inadequate for future commercial survival. Instead, extensible, closed-loop and potentially automated high-density cell amplification technologies are needed.

SUMMARY

The present invention is intended to provide a method for non-enzymatic 3D culture and amplification of MSCs, which uses a temperature-responsive intelligent material to prepare a microcarrier, so that MSCs are subjected to non-enzymatic 3D culture and amplification under an action of a stirred tank bioreactor.

To achieve the aforesaid purposes, the present invention provides a method for non-enzymatic 3D culture and amplification of MSCs, including the following steps:
  S1, preparing poly(lactic-co-glycolic acid) (PLGA) porous microspheres;
  S2, preparing a PLGA-PEG-PLGA thermosensitive coating microcarrier (PEG is polyethylene glycol);
  S3, culturing and amplifying MSCs; and
  S4, performing non-enzymatic separation of the MSCs: reducing a culture temperature to below a critical phase transition temperature, and centrifuging a culture medium to collect stem cells.

Preferably, in S1, the method for preparing PLGA porous microspheres includes the following steps:
  (1) dissolving PLGA, cholesterol and $NH_4HCO_3$ in ether at a weight ratio of (10:1:1)-(10:2:2) at a room temperature, adding water to the mixture ether solution, and performing ultrasonication for 15-40 min to form a water-in-oil (W/O) emulsion; and
  (2) performing spray drying on the emulsion obtained in S1 by a spray dryer to form PLGA porous microspheres.

Preferably, in S1 a volume ratio of the water added to the ether is (3:1)-(4:1).

Preferably, in S2, the method for preparing a PLGA-PEG-PLGA thermosensitive coating microcarrier includes the following steps:
  a. preparing a 10-15 wt % PLGA-PEG-PLGA aqueous solution at 25° C., adding the dried PLGA porous microspheres to the PLGA-PEG-PLGA aqueous solution, and stirring the resulting solution for 15-20 min; and
  b. centrifuging the resulting solution from step a to obtain the PLGA-PEG-PLGA thermosensitive coating microcarrier, and preserving the PLGA-PEG-PLGA thermosensitive coating microcarrier at 37° C. for later use.

Preferably, in step 3, the method for culturing and amplifying MSCs includes the following steps:
  (1) mixing MSCs extracted from a bone marrow with the thermosensitive coating PLGA porous microspheres in a non-heterologous culture medium, and placing the mixed solution in a stirred tank bioreactor; and
  (2) adjusting a reaction temperature to 37° C., continuously supplying oxygen, and stirring and mixing the mixed solution for 1-3 d; wherein the cells are amplified on the microcarrier.

Preferably, in S4, the culture temperature is 30-34° C.

Therefore, the present invention adopts the method for non-enzymatic 3D culture and amplification of MSCs, wherein the PLGA porous microspheres have a very high surface area and are easy to disperse in a culture medium, so in animal cell culture, a 3D porous structure, an appropriate spatial structure and porosity on their surfaces are conducive to adhesion, growth and amplification of stem cells. As a carrier of cell culture, the microspheres can provide a large amount of specific surface area for cells to be produced on the surfaces; as a carrier of animal cell culture, the microspheres can realize high-density culture of cells in a limited space, with simple control and excellent reproducibility.

PLGA-PEG-PLGA is a thermosensitive phase transition hydrogel. Using the thermosensitive hydrogel to form a hydrogel layer on a surface of a microcarrier will reduce cumbersome steps of downstream separation, so as to rapidly separate stem cells for use in tissues that require direct implantation. After culture, the surface of the microcarrier can be dispersed by temperature changes and free MSCs can be collected therein without enzyme solution separation.

The present invention features a high space efficiency, high yield, high economic efficiency, etc., and provides a new idea for commercial amplification of stem cells.

The technical solutions of the present invention will be further described below in detail in combination with the accompanying drawings and embodiments.

DETAILED DESCRIPTION OF THE PREFERRED EMBODIMENTS

Figure 1:
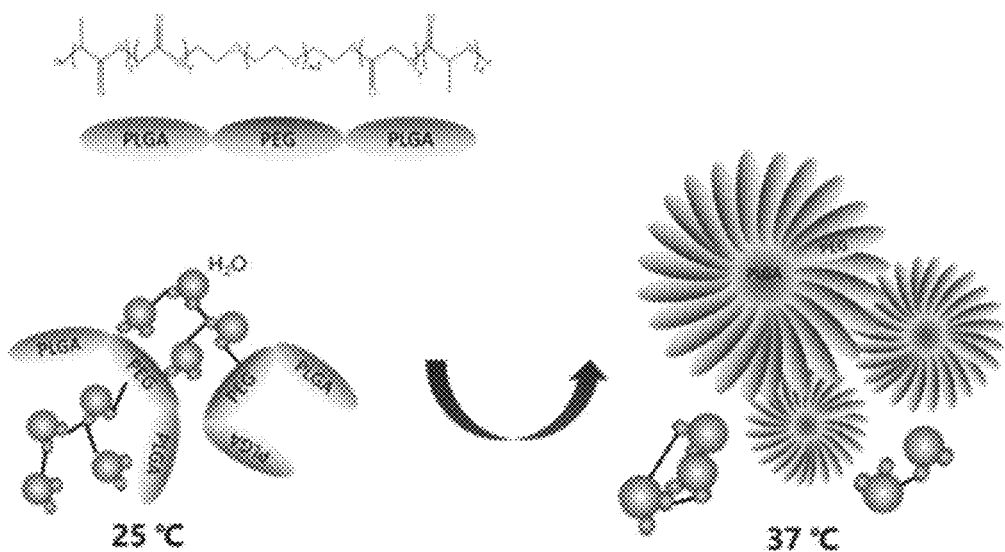
FIG. 1 shows phase transition mechanisms of a hydrogel coating.

The technical solutions of the present invention will be further described below in combination with the accompanying drawings and embodiments.

Unless otherwise defined, the technical or scientific terms used herein should have ordinary meanings understood by those of ordinary skill in the art of the present invention.

It is apparent to those skilled in the art that the present invention is not limited to the details of the above-mentioned exemplary embodiments and can be realized in other specific forms without departing from the intention or essential features of the present invention. Therefore, in all respects, the embodiments should be considered to be exemplary and non-restrictive. The scope of the present invention is limited by the appended claims rather than the above-mentioned description, so that all changes falling within the meaning and scope of the equivalents of the claims are intended to be included in the present invention, and any accompanying drawing marks in the claims should not be deemed to limit the claims involved.

Moreover, it should be understood that although the specification is described according to the implementation modes, not each implementation mode contains only one independent technical solution. This narrative form of the specification is for the sake of clarity only. Those skilled in the art should take the specification as a whole, and the technical solutions in various embodiments may be combined appropriately to form other implementation modes that can be understood by those skilled in the art. These other implementation modes should also fall within the protection scope of the present invention.

In addition, it should be understood that the above-mentioned specific embodiments are used for explaining the present invention only, and the protection scope of the present invention is not limited to such specific embodiments. Within the technical scope disclosed by the present invention, the equivalent substitutions or changes made by those skilled in the art based on the technical solutions and inventive concept of the present invention should fall within the protection scope of the present invention/invention.

The "including/comprising" or "containing" and similar words used herein refer to that the element ahead of the word covers the elements listed behind the word and does not exclude the possibility of covering other elements as well. The orientations or position relations indicated by terms "inside", "outside", "up" and "down" are those shown based on the accompanying drawings, only used for the convenience of describing the present invention and simplifying the description, rather than indicating or implying that the device or element referred to must have a particular orientation or be constructed and operated in a particular orientation, so they cannot be understood as a limitation to the present invention. When the absolute position of the object described changes, the relative position relation may also change accordingly. In the present invention, unless otherwise expressly specified and limited, the term "attaching" should be understood in a broad sense. For example, two elements may be connected fixedly, connected detachably, or integrated; two elements may be connected directly, or connected indirectly through an intermediate medium, or communicated internally or interact. Those of ordinary skill in the art can understand the specific meanings of such terms in the present invention according to the specific situations. The term "about" used herein has the meaning known to those skilled in the art, and preferably refers to that the value modified by the term is within the range of +50%, ±40%, ±30%, ±20%, +10%, 5% or ±1%.

All terms (including technical or scientific terms) used in the disclosure have the same meanings as those understood by those of ordinary skill in the art of the disclosure, unless otherwise specifically defined. Moreover, it should be understood that terms defined in a general dictionary should be understood to have meanings consistent with those in the context of the relevant techniques, and should not be interpreted in an idealized or highly formal sense, unless expressly defined herein.

The techniques, methods and equipment known to those of ordinary skill in the art may not be discussed in detail, but where appropriate, such techniques, methods and equipment should be considered as a part of the specification.

The contents disclosed in the prior art literature referenced in the specification of the present invention are incorporated herein by reference in its entirety.

Example 1

A method for preparing PLGA porous microspheres included the following steps:
(1) PLGA, cholesterol and $NH_3HCO_3$ were dissolved in ether at a ratio of 10:1:1 by weight at a room temperature, water was added to the mixture ether solution (a volume ratio of water:ether was 3:1), and ultrasonication was performed for 30 min to form a water-in-oil (W/O) emulsion; and
(2) such emulsion was subjected to spray drying by a spray dryer to form PLGA porous microspheres.

Example 2

A method for preparing a PLGA-PEG-PLGA thermosensitive coating microcarrier included the following steps:
(1) a 10-15 wt %/o PLGA-PEG-PLGA aqueous solution was prepared at 25° C., the dried PLGA porous microspheres were added to the PLGA-PEG-PLGA aqueous solution, and the resulting solution was stirred for 15-20 min; and
(2) the resulting solution was centrifuged to obtain the PLGA-PEG-PLGA thermosensitive coating microcarrier, and the PLGA-PEG-PLGA thermosensitive coating microcarrier was preserved at 37° C. for later use.

Figure 2:
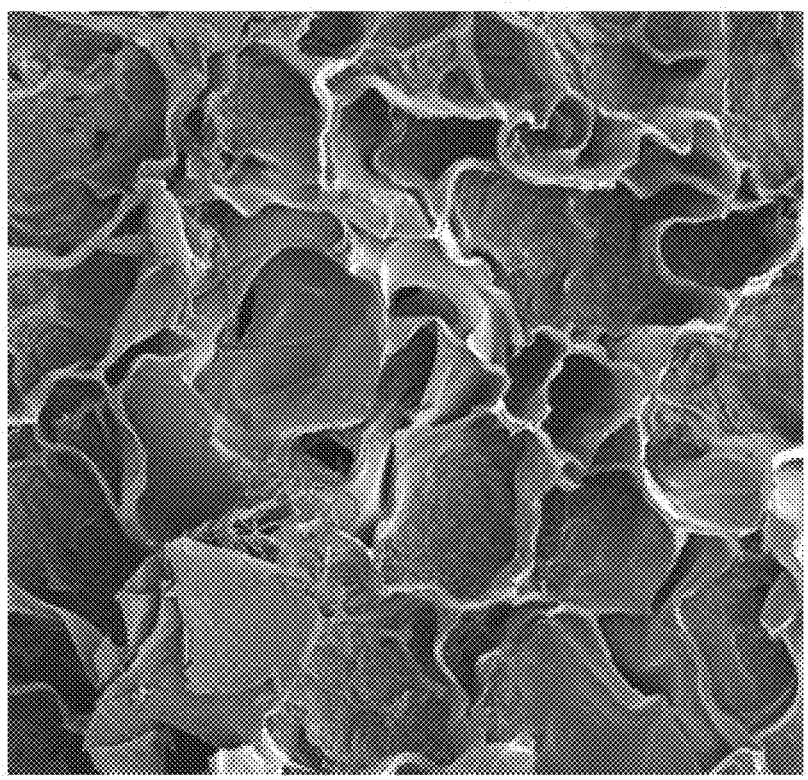
FIG. 2 shows a scanning electron microscope (SEM) image of a thermosensitive gel coating on a surface of a microcarrier.
Figure 3:
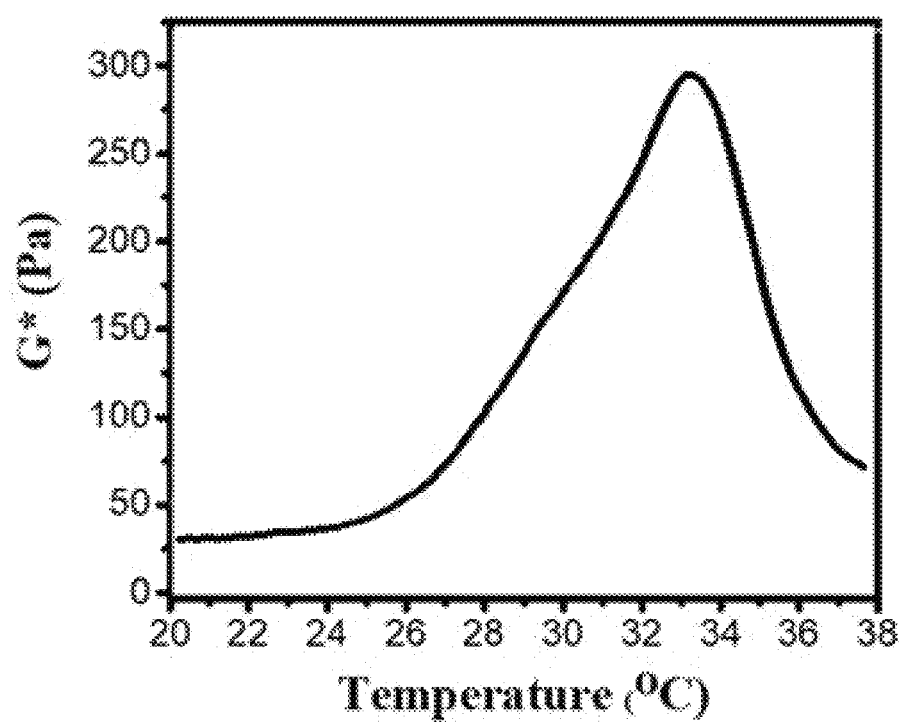
FIG. 3 shows rheology results of a thermosensitive gel coating on a surface of a microcarrier.

A SEM image and rheology results of a thermosensitive gel coating on a surface of the microcarrier are as shown in FIG. 2 and FIG. 3.

Example 3

Culture and amplification of MSCs:
(1) MSCs extracted from a bone marrow were mixed with the thermosensitive coating PLGA porous microspheres in a non-heterologous culture medium, and the mixed solution was placed in a stirred tank bioreactor; and
(2) a reaction temperature was adjusted to 37° C., oxygen was continuously supplied, and the mixed solution was stirred and mixed for 1-3 d; the cells were amplified on the microcarrier.

Example 4

Non-enzymatic separation of MSCs: A culture temperature was reduced to 30° C., and cultural supernatant was extracted and centrifuged for 10 min at 1,500 rpm to collect stem cells.

Therefore, the present invention adopts the method for non-enzymatic 3D culture and amplification of MSCs, wherein the PLGA porous microspheres as a carrier of cell culture can provide a large amount of specific surface area for cells to be produced on the surfaces, and can realize high-density culture of cells in a limited space, with simple control and excellent reproducibility. Moreover, the thermosensitive hydrogel coating reduces cumbersome steps of downstream separation and requires no additional enzymolysis process, so that stem cells are efficiently amplified and separated for cell therapy.

Finally, it should be stated that the above-mentioned embodiments are only used for describing, rather than limiting, the technical solutions of the present invention. Although the present invention is described in detail by reference to the preferred embodiments, those of ordinary skill in the art should understand that they can still make modifications or equivalent substitutions to the technical solutions of the present invention, but these modifications or equivalent substitutions will not make the modified technical solutions deviate from the spirit and scope of the technical solutions of the present invention.

What is claimed is:

1. A method for non-enzymatic 3D culture and amplification of mesenchymal stem cells (MSCs), comprising the following steps:
   S1) preparing poly(lactic-co-glycolic acid) (PLGA) porous microspheres, wherein preparing the PLGA porous microspheres comprises the following steps:
   S1a) dissolving PLGA, cholesterol, and $NH_3HCO_3$ in ether at a weight ratio of (10:1:1)-(10:2:2) at a room temperature to obtain an ether mixture,
   adding water to the ether mixture, wherein a volume ratio of the water added to the ether is (3:1)-(4:1), and performing ultrasonication for 15-40 min to form a water-in-oil (W/O) emulsion; and
   S1b) performing spray drying on the W/O emulsion obtained in step (S1a) by a spray dryer to form the PLGA porous microspheres;
   S2) preparing a PLGA-PEG-PLGA thermosensitive coating microcarrier, wherein PEG is polyethylene glycol;
   S3) culturing and amplifying the MSCs; and
   S4) performing non-enzymatic separation of the MSCs: reducing a culture temperature to below a critical phase transition temperature, and centrifuging a culture medium to collect the MSCs.

2. The method according to claim 1, wherein in step S2, the preparing the PLGA-PEG-PLGA thermosensitive coating microcarrier comprises the following steps:
   S2a) preparing a 10-15 wt % PLGA-PEG-PLGA aqueous solution at 25° C., then adding the PLGA porous microspheres dried in step 1 to the 10-15 wt % PLGA-PEG-PLGA aqueous solution, and stirring a resulting solution for 15-20 min; and
   S2b) centrifuging the resulting solution obtained from step S2a to obtain the PLGA-PEG-PLGA thermosensitive coating microcarrier and preserving the PLGA-PEG-PLGA thermosensitive coating microcarrier at 37° C. for later use.

3. The method according to claim 1, wherein in step S3, the culturing and amplifying the MSCs comprises the following steps:
   S3a) mixing the MSCs extracted from a bone marrow with thermosensitive coating PLGA porous microspheres in a non-heterologous culture medium to obtain a mixed solution, and placing the mixed solution in a stirred tank bioreactor; and
   S3b) adjusting a reaction temperature to 37° C., and stirring and mixing the mixed solution for 1-3 days, wherein the MSCs are amplified on the thermosensitive coating PLGA porous microspheres.

4. The method according to claim 1, wherein in step S4, the culture temperature is 30-34° C.

* * * * *